United States Patent [19]

Müller et al.

[11] Patent Number: 4,629,733
[45] Date of Patent: Dec. 16, 1986

[54] INDOLINONES AND PHARMACEUTICAL COMPOSITIONS CONTAINING SAME

[75] Inventors: Erich Müller; Josef Nickl; Josef Roch; Berthold Narr, all of Biberach, Fed. Rep. of Germany

[73] Assignee: Dr. Karl Thomae GmbH, Biberach an der Riss, Fed. Rep. of Germany

[21] Appl. No.: 625,020

[22] Filed: Jul. 27, 1984

Related U.S. Application Data

[63] Continuation of Ser. No. 319,913, Nov. 10, 1981, abandoned.

[30] Foreign Application Priority Data

Nov. 12, 1980 [DE] Fed. Rep. of Germany ....... 3042632

[51] Int. Cl.$^4$ ..................... A61K 31/40; C07D 209/34
[52] U.S. Cl. .................................. 514/418; 546/153; 546/172; 546/177; 546/273; 548/486
[58] Field of Search ............... 548/486, 486; 546/153, 546/172, 177, 273; 424/274, 258, 263; 514/312, 343, 418

[56] References Cited

U.S. PATENT DOCUMENTS 4,329,347 5/1982 Muller et al. ........................ 548/486
4,442,111 4/1984 Muller et al. ........................ 548/486

FOREIGN PATENT DOCUMENTS 2853314 6/1980 Fed. Rep. of Germany.

OTHER PUBLICATIONS

Chemical Abstracts, vol. 93, Abstract No. 220608q (1980).

Primary Examiner—Alton D. Rollins
Attorney, Agent, or Firm—Hammond & Littell, Weissenberger & Dippert

[57] ABSTRACT

The present invention relates to novel indolinones of the general formula

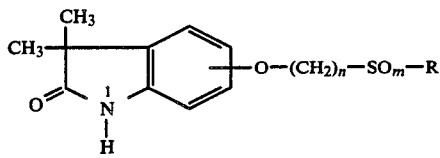

wherein R represents an aryl group having from 6 to 10 carbon atoms, unsubstituted or mono- or disubstituted by alkyl groups having from 1 to 5 carbon atoms, hydroxyl groups, alkoxy groups having from 1 to 3 carbon atoms, or halogen atoms, whereby the substituents may be the same or different and whereby the phenyl nucleus of the aryl group may also be substituted by an amino group, a hydroxyl group, or an alkanoylamino group with altogether from 1 to 3 carbon atoms; an aryl group having from 6 to 10 carbon atoms, substituted by 3 or 4 alkyl groups having from 1 to 5 carbon atoms each; a phenyl group substituted by a phenyl, halogenphenyl, or cycloalkyl group with 5 to 7 carbon atoms; an aralkyl group having from 7 to 11 carbon atoms; or a pentamethylphenyl, pyridyl, or quinolyl group; m represents the number 0, 1, or 2; and n represents the number 2, 3, 4, 5, or 6.

7 Claims, No Drawings

INDOLINONES AND PHARMACEUTICAL COMPOSITIONS CONTAINING SAME

This application is a continuation of copending U.S. patent application Ser. No. 319,913 filed Nov. 10, 1981 abandoned.

The present invention relates to novel indolinones of the general formula

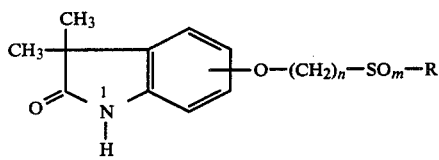

wherein
R represents an aryl group having from 6 to 10 carbon atoms, unsubstituted or mono- or disubstituted by alkyl groups having from 1 to 5 carbon atoms, hydroxyl groups, alkoxy groups having 1 to 3 carbon atoms, or halogen atoms, whereby the substituents may be the same or different and whereby the phenyl nucleus of the aryl group may also be substituted by an amino group, a hydroxyl group, or an alkanoylamino group with altogether from 1 to 3 carbon atoms; an aryl group having from 6 to 10 carbon atoms, substituted by 3 or 4 alkyl groups having from 1 to 5 carbon atoms each; a phenyl group substituted by a phenyl, halogenphenyl, or cycloalkyl group having from 5 to 7 carbon atoms; an aralkyl group having from 7 to 11 carbon atoms; or a pentamethylphenyl, pyridyl, or quinolyl group;
m represents the number 0, 1 or 2; and
n represents the number 2, 3, 4, 5, or 6,
as well as to processes for their preparation, and to pharmaceutical compositions containing them. The compounds of Formula I demonstrate valuable pharmacological properties, especially an antithrombotic activity and an inhibiting activity with regard to phosphodiesterase and to tumor metastasis.

The expression "halogen atom" in the definition of the radical R especially has the meaning fluorine, chlorine, bromine, or iodine atom. Similarly, a "halogen" substituent is particularly a fluoro, chloro, bromo, or iodo group. Moreover, the radical R may, for example, comprise one of the following groups:
phenyl, methylphenyl, ethylphenyl, isopropylphenyl, tert.butylphenyl, tert.pentylphenyl, cyclopentylphenyl, cyclohexylphenyl, cycloheptylphenyl, biphenylyl, fluoro-biphenylyl, chlorobiphenylyl, bromo-biphenylyl, aminophenyl, formylaminophenyl, acetylaminophenyl, propionylaminophenyl, hydroxyphenyl, methoxyphenyl, ethoxyphenyl, propoxyphenyl, fluorophenyl, chlorophenyl, bromophenyl, iodophenyl, dimethylphenyl, trimethylphenyl, tetramethylphenyl, pentamethylphenyl, methylethylphenyl, methylisopropylphenyl, methyl-tert.butylphenyl, diisopropylphenyl, triisopropylphenyl, dimethoxyphenyl, difluorophenyl, dichlorophenyl, dibromophenyl, methylchlorophenyl, methyl-bromophenyl, chloro-bromophenyl, chloromethoxyphenyl, bromo-methoxyphenyl, dichloroaminophenyl, dibromoaminophenyl, chloro-bromoamihophenyl, dimethylhydroxyphenyl, diisopropyl-hydroxyphenyl, di-tert.butylhydroxyphenyl, naphthyl, methoxynaphthyl, propoxynaphthyl, dimethoxynaphthyl, benzyl, phenylethyl, phenylpropyl, naphthylmethyl, pyridyl, or quinolyl.

Preferred compounds of the Formula I are, however, those
wherein
R represents a phenyl group, which may be substituted by a hydroxyl, amino, acetylamino, cyclohexyl, phenyl, or fluorophenyl group; a phenyl group mono- or disubstituted by halogen atoms, methoxy groups, or alkyl groups having from 1 to 4 carbon atoms, whereby the substituents of the phenyl nucleus may be the same or different; a phenyl group substituted by 3, 4, or 5 methyl groups; an aminophenyl or hydroxyphenyl group substituted by two halogen atoms or by two alkyl groups having from 1 to 4 carbon atoms; a naphthyl group optionally substituted by one or two methoxy groups; or a benzyl, pyridyl, or quinolyl group;
m represents the number 0, 1, or 2; and
n represents the number 2, 3, 4, or 5,
especially, the compounds of the general formula

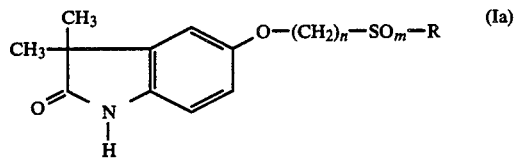

wherein
R, m, and n are as defined above.

Particularly preferred compounds of Formula Ia are those
wherein
R represents a phenyl, 4-chlorophenyl, 4-tert.butylphenyl, 4-methoxyphenyl, 4-(2'-fluorophenyl)-phenyl, 4-cyclohexylphenyl, 3,4-dichlorophenyl, 3,4-dimethoxyphenyl, 3,5-dibromo-4-aminophenyl, 3,5-dichloro-4-hydroxyphenyl, 3,5-di-tert.butyl-4-hydroxyphenyl, naphthyl-(2), or 6,7-dimethoxynaphthyl-(2) group;
m represents the number 0, 1, or 2; and
n represents the number 4.

According to the invention the novel compounds can be obtained according to the following procedures:

METHOD A

A hydroxyl-substituted compound of the general formula

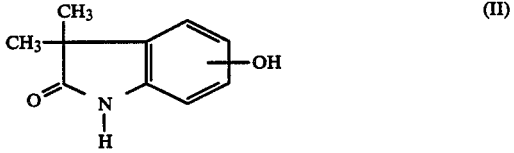

or a salt thereof with an inorganic or tertiary organic base, is reacted with a compound of the general formula

wherein R, m and n are as defined above, and Z represents a nucleophilic exchangeable group such as a halogen atom or a sulfonic acid ester radical, for example, a chlorine, bromine, or iodine atom or a p-toluene sulfonyloxy or methane sulfonyloxy group. The reaction is appropriately carried out in a suitable solvent such as 1,4-dioxane, tetrahydrofuran, chloroform, or toluene, preferably, however, in an anhydrous aprotic solvent such as acetone, dimethylformamide, or dimethylsulfoxide, optionally in the presence of an alkali metal base such as sodium carbonate, potassium carbonate, or sodium hydroxide, at temperatures between 0° C. and the boiling temperature of the solvent used, for example, at temperatures of from 0° to 100° C., preferably, however, at temperatures of from 10° to 50° C. The reaction can, however, be carried out without a solvent.

METHOD B

For the preparation of compounds of Formula I, wherein m represents the number 1 or 2, a compound of the general formula

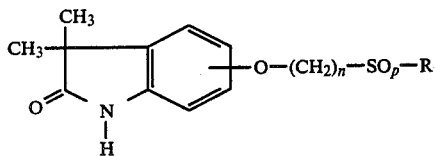
(IV)

wherein R and n are as defined above and p represents the number 0 or 1, is oxidized. The oxidation is preferably carried out in a solvent, for example, water, water/pyridine, ethanol, methanol, acetone, glacial acetic acid, formic acid, dilute sulfuric acid, or trifluoroacetic acid, dependent upon the oxidation agent used, appropriately at temperatures of from $-80°$ to $100°$ C.

For the preparation of compounds of Formula I wherein m represents the number 1, the oxidation is appropriately carried out with an equimolar amount of the oxidation agent employed, for example, with hydrogen peroxide in glacial acetic acid or formic acid at from 0° to 20° C. or in acetone at from 0° to 60° C., with a peracid such as performic acid in glacial acetic acid or trifluoroacetic acid at from 0° to 50° C., with sodium metaperiodate in aqueous methanol or ethanol at from 15° to 25° C., with N-bromo-succinimide in ethanol, with tert.butyl-hypochlorite in methanol at from $-80°$ to $-30°$ C., with iodobenzene dichloride in aqueous pyridine at from 0° to 20° C., with chromic acid in glacial acetic acid or in acetone at from 0° to 20° C., or with sulfuryl chloride in methylene chloride at $-70°$ C. The thioether-chlorocomplex obtained hereby is appropriately hydrolyzed with aqueous ethanol.

To prepare compounds of Formula I wherein m represents the number 2, the oxidation is appropriately carried out with one or two or more equimolar amounts of the oxidation agent employed, for example, with hydrogen peroxide in glacial acetic acid or in formic acid at from 20° to 100° C. or in acetone at from 0° to 60° C., with a peracid such as performic acid or m-chloroperbenzoic acid in glacial acetic acid, trifluoroacetic acid, or chloroform at temperatures of from 0° to 50° C., with nitric acid in glacial acetic acid at from 0° to 20° C., or with chromic acid or potassium permanganate in glacial acetic acid, water/sulfuric acid, or acetone at from 0° to 20° C. If in a compound of Formula IV p represents the number 0, the reaction is preferably carried out with two or more equimolar amounts of the corresponding oxidation agent; likewise, if p represents the number 1, the reaction is preferably carried out with at least one equimolar amount, or equivalent, of the corresponding oxidation agent.

METHOD C

To prepare the compound of Formula I wherein m represents the number 0 or 2, a compound of the general formula

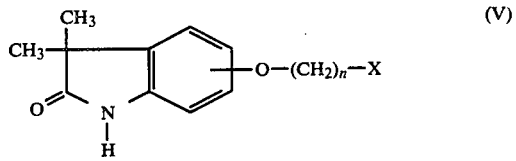
(V)

wherein n is as defined above and X represents a nucleophilic exchangeable group such as a halogen atom or a sulfonic acid ester radical, for example, a chlorine, bromine, or iodine atom, or a p-toluene sulfonyloxy or methane sulfonyloxy group, is reacted with a compound of the general formula $$Y-R \qquad (VI)$$

wherein R is as defined above and Y represents a MeSO$_2$-group, whereby Me represents an alkali metal such as sodium or potasium, an alkaline earth metal/2 atom such as the calcium/2 atom, or mercapto group. The reaction can be carried out in a suitable solvent such as 1,4-dioxane, tetrahydrofuran, chloroform, or toluene, preferably, however, in an anhydrous aprotic solvent such as acetone, dimethylformamide, or dimethylsulfoxide, optionally in the presence of an alkali metal base such as sodium carbonate, potassium carbonate, or sodium hydroxide, at temperatures between 0° C. and the boiling temperature of the solvent used, for example, at temperatures of from 0° to 100° C., preferably, however, at temperatures of from 10° to 50° C. The reaction can, however, be carried out without a solvent.

The compounds of Formulas II to VI used as starting materials are known in part from the literature or they can be obtained according to known procedures. For example, 5-hydroxy-indolinone-2 of Formula II can be obtained by melting α-bromo-isobutyric acid-p-phenetidide with a mixture of aluminium chloride, potassium chloride, and sodium chloride, and a compound of Formula IV or V can be obtained by reaction of a corresponding hydroxy-indolinone-2 with a corresponding monohalogen or dihalogen compound, respectively.

As mentioned above, the compounds of Formula I prepared according to the invention, possess—at a good oral resorption—valuable pharmacological properties, especially antithrombotic activities, and a PDE-inhibiting effect and an inhibiting effect on the aggregation of tumor cells (tumor metastasis). For example, the following compounds were tested with regard to their biological properties:

A=3,3-Dimethyl-5-(4-phenylsulfinyl-butoxy)-indolinone-2,
B=3,3-Dimethyl-5-[4-(3,4-dichlorophenylsulfinyl)-butoxy]-indolinone-2,
C=3,3-Dimethyl-5-[4-(4-cyclohexylphenylmercapto)-butoxy]-indolinone-2,
D=3,3-Dimethyl-5-[4-(2'-fluoro-4-biphenylylsulfinyl)-butoxy]-indolinone-2,
E=3,3-Dimethyl-5-[4-(3,4-dimethoxyphenylsulfinyl)-butoxy]-indolinone-2, F=3,3-Dimethyl-5-[4-(6,7-dimethoxy-naphthyl-(2)-sulfonyl)butoxy]-indolinone-2,
G=3,3-Dimethyl-5-[4-(3,5-di-tert.butyl-4-hydroxy-phenylsulfinyl)-butoxy]-indolinone-2,
H=3,3-Dimethyl-5-[4-(3,5-di-tert.butyl-4-hydroxy-phenylsulfonyl)-butoxy]-indolinone-2,
I=3,3-Dimethyl-5-[4-(4-methoxyphenyl-sulfinyl)-butoxy]-indolinone-2,
K=3,3-Dimethyl-5-[4-(4-tert.butyl-phenyl-sulfinyl)-butoxy]-indolinone-2,
L=3,3-Dimethyl-5-[4-(6,7-dimethoxy-naphthyl-(2)-sulfinyl)butoxy]-indolinone-2,
M=3,3-Dimethyl-5-[4-(3,5-dichloro-4-hydroxy-phenyl-mercapto)-butoxy]-indolinone-2,
N=3,3-Dimethyl-5-[4-(3,5-dibromo-4-amino-phenyl-sulfinyl)butoxy]-indolinone-2,
O=3,3-Dimethyl-5-[4-(naphthyl-(2)-sulfinyl)-butoxy]-indolinone-2,
P=3,3-Dimethyl-5-[4-(4-chlorophenylsulfinyl)-butoxy]-indolinone-2,
Q=3,3-Dimethyl-5-[5-(4-cyclohexyl-phenyl-sulfinyl)-pentoxy]-indolinone-2,
R=3,3-Dimethyl-5-[4-(4-tert.butyl-phenyl-sulfonyl)-butoxy]-indolinone-2, and
S=3,3-Dimethyl-5-[4-(4-cyclohexyl-phenyl-sulfinyl)-butoxy]-indolinone-2.

1. Determination of the prolongation of bleeding time

Preliminary remarks

The human organism as well as other warm-blooded animals have an ingenious mechanism which protects them from blood loss in case of injury. This system consists of blood platelets (thrombocytes), which quickly seal the injured vessels by means of their adhesiveness (*primary hemostasis*). Besides this cellular hemostatic mechanism, the body has a blood coagulation system. In this system plasma factors (proteins) are activated whereby plasma fibrinogen is converted to a fibrin coagulum. The system of primary hemostasis, mainly due to thrombocytes, and the coagulation system complement each other, both having the aim of protecting the body effectively from blood loss.

With some diseases it is found that coagulation and throbocyte aggregation also take place in intact blood vessels. The influence on the coagulation system of cumarine and heparine is known and can easily be measured by coagulation loss, the coagulation time being prolonged under the influence of these substances. (Plasms-recalcif. time, Quick-Test, Thrombin time, etc.).

The normality of the thrombocytes can be determined by measuring the bleeding time. The normal bleeding time in human beings is in the range of from 1 to 3 minutes and requires intact thrombocytes in a sufficient number. If the number of thrombocytes is normal and the bleeding time is prolonged, this signifies an abnormality in the thrombocytes. This is found in some inborn errors of thrombocyte-function. If, on the other hand, it is desired to prevent spontaneous aggregation of the thrombocytes and occlusion in the arterial system by antiplatelet drugs, the bleeding time should be prolonged as a consequence. Therefore, using antiplatelet substances, a prolongation of the bleeding time is expected. If the plasma coagulation system is not influenced by such a substance, coagulation tests will give a normal result.

Literature: W. D. Keidel: Kurzgefasstes Lehrbuch der Physiologie, George Thieme Verlag Stuttgart 1967, page 31: The Proceeding of Hemostasis.

METHOD

To measure the bleeding time, 10 mg/kg of the test compound is administered orally to conscious mice. After one hour 0.5 mm of the tip of the tail of the mouse is cut off, and the droplets of blood are gently removed with filter paper every 30 seconds. The number of drops of blood give a measure of the bleeding time (5 animals/experiment). The values in the following table represent the prolongation as a percentage as compared to a control group:

TABLE I

| Compound | Prolongation of Bleeding Time after One Hour (%) |
| --- | --- |
| B | 59 |
| D | >249 |
| E | >198 |
| F | >232 |
| G | 154 |
| H | 149 |
| I | >214 |
| K | >285 |
| L | 102 |
| M | 140 |
| N | >254 |
| O | 127 |
| P | 114 |
| Q | >174 |
| R | >242 |
| S | 104 |

2. PDE inhibition

Principle cAMP is hydrolysed to AMP by phosphodiesterase (PDE) from various sources, including blood platelets. This hydrolysis is inhibited by PDE inhibitors according to the concentration.

METHOD

The phosphodiesterase used is the 10,000×g supernatant of human blood platelets which have been frozen with water and thawed out again. An amount of 0.3 ml of a mixture which contains 0.1 mol/liter of trihydroxy-aminomethane (pH 7.4), 3 mmol/liter of magnesium chloride, 1 mmol/liter of AMP, 1 μmol/liter of $^3$H-cAMP (specific activity about 10 MBq/μmol), PDE as well as the substance to be tested, and water for the control is incubated for 15 minutes at 37° C. The incubation is stopped by the addition of 0.5 ml of zinc sulphate (0.266 mol/liter) and 0.5 ml of barium hydroxide (0.226 mol/liter), the precipitate is centrifuged, and the activity remaining in the supernatant of the unreacted $^3$H-cAMP is determined. From a comparison of the substance preparations and the control preparations, the concentration for a 50% inhibiting activity (IC$_{50}$) of the respective substance was calculated. The results are set forth in the following table:

TABLE II

| Substance | IC$_{50}$ (μMol/liter) |
| --- | --- |
| A | 2.50 |
| B | 0.30 |
| C | 2.50 |
| D | 0.027 |
| E | 0.54 |
| F | 0.24 |

TABLE II-continued

| Substance | IC$_{50}$ ($\mu$Mol/liter) |
| --- | --- |
| G | 0.07 |
| H | 0.059 |
| I | 0.50 |
| K | 0.27 |
| L | 0.24 |
| N | 0.11 |
| O | 0.11 |
| P | 0.36 |
| Q | 0.38 |
| R | 0.24 |
| S | 0.058 |

3. Acute toxicity

The acute toxicity of the substances to be tested was determined in groups of 5 mice each each after peroral administration of a dose of 250 mg/kg or 1000 mg/kg (observation time: 14 days). The results were as follows:

TABLE III

| Substance | Acute toxicity per os |
| --- | --- |
| A | 250 mg/kg (0 out of 5 animals died) |
| B | 1000 mg/kg (0 out of 6 animals died) |
| C | 1000 mg/kg (0 out of 6 animals died) |
| D | 1000 mg/kg (0 out of 6 animals died) |
| E | 1000 mg/kg (0 out of 6 animals died) |
| F | 1000 mg/kg (0 out of 6 animals died) |
| G | 1000 mg/kg (0 out of 6 animals died) |
| H | 1000 mg/kg (0 out of 6 animals died) |
| I | 1000 mg/kg (0 out of 6 animals died) |
| K | 1000 mg/kg (0 out of 6 animals died) |
| L | 1000 mg/kg (0 out of 6 animals died) |
| M | 1000 mg/kg (0 out of 6 animals died) |
| N | 1000 mg/kg (0 out of 6 animals died) |
| O | 1000 mg/kg (0 out of 6 animals died) |
| P | 1000 mg/kg (0 out of 6 animals died) |
| Q | 1000 mg/kg (0 out of 6 animals died) |
| R | 1000 mg/kg (0 out of 6 animals died) |
| S | 1000 mg/kg (0 out of 6 animals died) |

Due to their pharmacological properties the new compounds of Formula I are suitable for the prophylaxis of thromboembolic diseases such as, for example, coronary infarct, cerebral infarct, so-called transient ischaemic attacks, and amaurosis fugax, as well as for the treatment of arteriosclerosis, and for the metastasis prophylaxis. For pharmaceutical purposes the compounds of the present invention are administered to warm-blooded animals perorally, parenterally, topically, or rectally as active ingredients in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsions, ointments, gels, creams, powders, and sprays. Advantageously the active ingredient or a mixture of the different active ingredients of Formula I may be administered to both humans or animals, in a single dose of from about 50 to 100 mg (0.67 to 1.33 mg/kg of body weight), preferably from about 60 to 80 mg (0.80 to 1.07 mg/kg of body weight), two to three times daily. A daily dose is therefore from about 100 to 300 mg (from about 1.33 to 4.0 mg/kg of body weight), preferably from about 120 to 240 mg (from about 1.6 to 3.2 mg/kg of body weight). Depending on the type and body weight of the patient to be treated, on the type and severity of the disease, on the type of preparation, and on the route of administration as well as on the period or interval over which the administration takes place, it may, however, be necessary to deviate from the above dosages. Thus, it may be sufficient in some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

The following examples are intended to illustrate the invention and should not be construed as limiting the invention thereto.

EXAMPLES

Preparation of the starting compounds

EXAMPLE 1

3,3-Dimethyl-5-(4-chlorobutoxy)-indolinone-2

(a) 3,3-Dimethyl-5-(4-acetoxy-butoxy)-indolinone-2

An amount of 150.6 gm (0.85 mol) of 3,3-dimethyl-5-hydroxy-indolinone-2 was added to a well stirred suspension of 117.5 gm (0.85 mol) of anhydrous potassium carbonate in 680 ml of sulfolane. After addition of 199.0 gm (1.2×0.85 mol) of 4-acetoxy-butylbromide the reaction mixture was warmed for 2.5 hours up to 85° to 90° C. After cooling to room temperature, an ice/water-mixture was stirred thereto, and the mixture was acidified with glacial acetic acid and diluted to 10 liters. After 2 hours the precipitated crystals were recovered by suction filtration, washed with water, and dried at room temperature in a circulation air drier. One sample was recrystallized from a mixture of cyclohexane/ethyl acetate (1:1). White crystals were obtained.

M.p.: 81°–84° C.

(b) 3,3-Dimethyl-5-(4-hydroxy-butoxy)-indolinone-2

The crystals obtained in step (a) were added under stirring to 1275 ml of methanol, and the mixture was reacted under external cooling with 425 ml (2.5×0.85 mol) of 5N sodium hydroxide solution, whereby the temperature did not exceed 18° C. After 40 minutes the red solution was neutralized with 5N hydrochloric acid and largely evaporated in a rotation evaporator. The oily residue was recrystallized from ethyl acetate under addition of a small amount of cyclohexanol.

M.p.: 112°–113° C.

Yield: 159.8 gm (75.4% of theory).

(c) 3,3-Dimethyl-5-(4-chlorobutoxy)-indolinone-2

An amount of 74.8 gm of 3,3-dimethyl-5-(4-hydroxybutoxy)-indolinone-2 was suspended in 1 liter of toluene, 0.9 liter of thionyl chloride was added, and then the reaction mixture was heated for 2 hours up to boiling. The volatile components were distilled off in vacuo in a rotation evaporator, and the residue was recrystallized from petroleum ether with addition of a small amount of ethyl acetate.

M.p.: 83.5°–85° C.

Yield: 64.2 gm (80% of theory).

EXAMPLE 2

3,3-Dimethyl-5-(5-bromopentoxy)-indolinone-2

An amount of 19.3 gm (4×0.07 mol) of anhydrous potassium carbonate and 12.4 gm (0.07 mol) of 3,3-dimethyl-5-hydroxy-indolinone-2 were added to 70 ml of anhydrous dimethylsulfoxide, and the mixture was stirred for 10 minutes. Subsequently 64.4 gm (4×0.07 mol) of 1,5-dibromopentane were added. After stirring for 18 hours, the reaction mixture was diluted with 350 ml of ice water and extracted with ethyl acetate. The extracts were evaporated, and the residue was chromatographed on a silica gel column with a mixture of cyclohexane and ethyl acetate (1:1). From the main fraction a crystalline substance was obtained.

M.p.: 80.5°–85.0° C.
Yield 14.9 gm (65.2% of theory).

EXAMPLE 3

3,3-Dimethyl-5-(3-chloropropoxy)-indolinone-2

The above compound was prepared analogously to Example 2 from 3,3-dimethyl-5-hydroxy-indolinone-2 and 1-chloro-3-bromopropane.

M.p.: 68°–70° C.
Yield 71% of theory.

EXAMPLE 4

3,3-Dimethyl-5-(2-chloroethoxy)-indolinone-2

The above compound was prepared analogously to Example 2 from 3,3-dimethyl-5-hydroxy-indolinone-2 and benzene sulfonic acid-2-chloroethyl ester.

M.p.: 151°–152° C.
Yield: 60% of theory.

Preparation of the final products

EXAMPLE 5

3,3-Dimethyl-5-[4-(3,4-chlorophenyl-sulfinyl)-butoxy]-indolinone-2

Quantities of 1.06 gm of 3,3-dimethyl-5-hydroxy-indolinone-2 (m.p.: 250°–253° C.) and 1.66 gm of potassium carbonate in 15 ml of dimethyl sulfoxide were stirred for 5 minutes. Subsequently, 1.98 gm of 4-(3,4-dichlorophenyl)-sulfinylbutylbromide were added, and the reaction mixture was stirred for 25 hours at room temperature. After acidification with 2N hydrochloric acid, the reaction mixture was extracted with 250 ml of ethyl acetate. The organic phase was washed twice, with approximately 50 ml of saturated sodium chloride solution each time, and dried over magnesium sulfate. After evaporation a colorless, viscous oil was obtained, which was chromatographed over a silica gel column by means of chloroform/ethanol (9:1). The evaporated eluate crystallized after standing for several days.

M.p.: 124°–125° C.
Yield: 1.85 gm (93.9% of theory).

EXAMPLE 6

3,3-Dimethyl-5-(4-phenylsulfinyl-butoxy)-indolinone-2

The above compound was prepared analogously to Example 5 from 3,3-dimethyl-5-hydroxy-indolinone-2 (m.p.: 250°–253° C.) and 4-phenyl-sulfinylbutyl-bromide. The product was a viscous oil. $R_f$ value: 0.35. (Silica gel; eluant: chloroform/ethanol (9:1)).

Yield: 91.4% of theory.

EXAMPLE 7

3,3-Dimethyl-5-[4-(4-cyclohexylphenylmercapto)-butoxy]-indolinone-2

An amount of 6.91 gm of 3,3-dimethyl-5-(4-chlorobutoxy)indolinone-2 was added under stirring to a mixture of 5.46 gm 4-cyclohexylthiophenyl, 7.13 gm of anhydrous potassium carbonate, and 60 ml of dimethylsulfoxide, and the mixture was stirred further for 45 minutes at room temperature. Subsequently, the reaction mixture was extracted with 500 ml of ethyl acetate, and the organic phase was washed 4 times, with 50 ml of water each time, to remove the dimethylsulfoxide and the inorganic salts. After drying over magnesium sulfate, the solvent was evaporated, and the residue was crystallized from cyclohexane.

M.p.: 113°–116° C.
Yield: 8.0 gm (73.2% of theory).

EXAMPLE 8

3,3-Dimethyl-5-[4-(4-cyclohexylphenyl-sulfinyl)-butoxy]-indolinone-2

A quantity of 5.46 gm (0.0129 mol) of 3,3-dimethyl-5-[4-(4-cyclohexylphenylmercapto)-butoxy]-indolinone-2 was suspended in 50 ml of glacial acetic acid and reacted under stirring with 1.16 ml (1.05×0.0129 mol) of hydrogen peroxide (397.4 mg/ml), which was dissolved in 12 ml of glacial acetic acid. After 5 minutes the solution was clear, and after 85 minutes the reaction was finished at room temperature. The reaction solution was poured into ethyl acetate and extracted with enough 20% soda solution to provide an alkaline solution. The aqueous phase was separated, the organic phase was dried over magnesium sulfate, and the solvent was distilled off. The residue was recrystallized from cyclohexane with addition of a small amount of ethyl acetate.

M.p.: 125°–126° C.
Yield: 4.67 gm (82.4% of theory).

EXAMPLE 9

3,3-Dimethyl-5-[4-(4-cyclohexylphenyl-sulfonyl)-butoxy]-indolinone-2

An amount of 0.439 gm (0.001 mol) of 3,3-dimethyl-5-[4-(4-cyclohexylphenyl-sulfinyl)-butoxy]-indolinone-2 was dissolved in 5 ml of formic acid and reacted with 0.086 ml (2.5×0.001 mol) of hydrogen peroxide (397.4 mg/ml). After 2.5 hours ethyl acetate was added, the reaction mixture was neutralized with 20% soda solution, and the ethyl acetate phase was dried over magnesium sulfate. The evaporation residue was recrystallized from cyclohexane with addition of a small amount of ethyl acetate.

M.p.: 153°–156° C.
Yield: 0.419 gm (92% of theory).

EXAMPLE 10

3,3-Dimethyl-5-[4-(3,5-dibromo-4-amino-phenylmercapto)butoxy]-indolinone-2

The above compound was prepared analogously to Example 7 from 3,3-dimethyl-5-(4-chlorobutoxy)-indolinone-2 and 4-amino-3,5-dibromo-thiophenol.

M.p.: 143.5°–145.5° C.
Yield: 66% of theory.

EXAMPLE 11

3,3-Dimethyl-5-[4-(3,5-dibromo-4-amino-phenyl-sulfinyl)-butoxy]-indolinone-2

The above compound was prepared analogously to Example 8 from 3,3-dimethyl-5-[4-(3,5-dibromo-4-aminophenyl-mercapto)butoxy]-indolinone-2 and hydrogen peroxide.

M.p.: 118.5°–119.5° C.
Yield: 64.9% of theory.

EXAMPLE 12

3,3-Dimethyl-5-[4-(3,5-dibromo-4-amino-phenylsulfonyl)butoxy]-indolinone-2

The above compound was prepared analogously to Example 9 from 3,3-dimethyl-5-[4-(3,5-dibromo-4-amino-phenylmercapto)butoxy]-indolinone-2 and hydrogen peroxide.

M.p.: 188°–191° C.
Yield 68.2% of theory.

EXAMPLE 13

3,3-Dimethyl-5-[4-(3-methyl-4-bromo-phenylmercapto)-butoxy]-indolinone-2

The above compound was prepared analogously to Example 7 from 3,3-dimethyl-5-(4-chlorobutoxy)-indolinone-2 and 3-methyl-4-bromo-thiophenol.
M.p.: 122°–124° C.
Yield: 82% of theory.

EXAMPLE 14

3,3-Dimethyl-5-[4-(3-methyl-4-bromo-phenylsulfinyl)-butoxy]-indolinone-2

The above compound was prepared analogously to Example 8 from 3,3-dimethyl-5-[4-(3-methyl-4-bromo-phenylmercapto)butoxy]-indolinone 2 and hydrogen peroxide.
M.p.: 121°–123° C.
Yield: 64% of theory.

EXAMPLE 15

3,3-Dimethyl-5-[4-(3-methyl-4-bromo-phenylsulfonyl)-butoxy]-indolinone-2

The above compound was prepared analogously to Example 9 from 3,3-dimethyl-5-[4-(3-methyl-4-bromo-phenylsulfinyl)-butoxy]-indolinone-2 and hydrogen peroxide.
M.p.: 142°–144° C.
Yield: 78% of theory.

EXAMPLE 16

3,3Dimethyl-5-[4-(2'-fluoro-4-biphenylyl-mercapto)-butoxy]-indolinone-2

The above compound was prepared analogously to Example 7 from 3,3-dimethyl-5-(4-chlorobutoxy)-indolinone-2 and 2'-fluoro-4-biphenylylmercaptan.
M.p.: 112°–113° C.
Yield: 50.3% of theory.

EXAMPLE 17

3,3-Dimethyl-5-[4-(2'-fluoro-4-biphenylyl-sulfinyl)-butoxy]-indolinone-2

The above compound was prepared analogously to Example 8 from 3,3-dimethyl-5-[4-(2'-fluoro-4-biphenylyl-mercapto)-butoxy]-indolinone-2 and hydrogen peroxide.
M.p.: 143°–145° C.
Yield: 85% of theory.

EXAMPLE 18

3,3-Dimethyl-5-[4-(2'-fluoro-4-biphenylyl-sulfonyl)-butoxy]-indolinone-2

The above compound was prepared analogously to Example 9 from 3,3-dimethyl-5-[4-(2'-fluoro-4-biphenylyl-mercapto)-butoxy]-indolinone-2 and hydrogen peroxide.
M.p.: 163°–164° C.
Yield: 77% of theory.

EXAMPLE 19

3,3-Dimethyl-5-[4-(4-tert.butyl-phenylmercapto)-butoxy]-indolinone-2

The above compound was prepared analogously to Example 7 from 3,3-dimethyl-5-(4-chloro-butoxy)-indolinone-2 and 4-tert.butylthiophenol.
M.p.: 115°–116° C.
Yield 86% of theory.

EXAMPLE 20

3,3-Dimethyl-5-[4-(4-tert.butyl-phenyl-sulfinyl)-butoxy]-indolinone-2

The above compound was prepared analogously to Example 8 from 3,3-dimethyl-5-[4-(4-tert.butyl-phenylmercapto)-butoxy]indolinone-2 and hydrogen peroxide.
M.p.: 156°–158° C.
Yield 87% of theory.

EXAMPLE 21

3,3-Dimethyl-5-[4-(4-tert.butyl-phenylsulfonyl)-butoxy]-indolinone-2

The above compound was prepared analogously to Example 9 from 3,3-dimethyl-5-[4-(4-tert.butyl-phenylmercapto)-butoxy]-indolinone-2 and hydrogen peroxide.
M.p.: 189°–191° C.
Yield: 77% of theory.

EXAMPLE 22

3,3-Dimethyl-5-[4-(3,5-dimethoxy-phenylmercapto)-butoxy]-indolinone-2

The above compound was prepared analogously to Example 7 from 3,3-dimethyl-5-(4-chloro-butoxy)-indolinone-2 and 3,4-dimethoxy-thiophenol.
M.p. 102°–105° C.
Yield: 70% of theory.

EXAMPLE 23

3,3-Dimethyl-5-[4-(3,4-dimethoxy-phenylsulfinyl)-butoxy]-indolinone-2

The above compound was prepared analogously to Example 8 from 3,3-dimethyl-5-[4-(3,4-dimethoxy-phenylmercapto)-butoxy]-indolinone-2 and hydrogen peroxide.
M.p.: 146°–148° C.
Yield: 85% of theory.

EXAMPLE 24

3,3-Dimethyl-5-[4-(3,4-dimethoxy-phenylsulfonyl)-butoxy]-indolinone-2

The above compound was prepared analogously to Example 9 from 3,3-dimethyl-5-[4-(3,4-dimethoxy-phenylsulfinyl)-butoxy]-indolinone-2 and hydrogen peroxide.
M.p.: 155°–156° C.
Yield: 81% of theory.

EXAMPLE 25

3,3-Dimethyl-5-[4-(6,7-dimethoxy-naphthyl-(2)-mercapto)-butoxy]-indolinone-2

The above compound was prepared analogously to Example 7 from 3,3-dimethyl-5-(4-chloro-butoxy)-indolinone-2 and 6,7-dimethoxy-thionaphthol-(2).
M.p.: 167°–169° C.
Yield: 74% of theory.

EXAMPLE 26

3,3-Dimethyl-5-[4-(6,7-dimethoxy-naphthyl-(2)-sulfinyl)-butoxy]-indolinone-2

The above compound was prepared analogously to Example 8 from 3,3-dimethyl-5-[4-(6,7-dimethoxy-naphthyl-(2)-mercapto)-butoxy]-indolinone-2 and hydrogen peroxide.
M.p.: 181°–182° C.
Yield: 84% of theory.

EXAMPLE 27

3,3-Dimethyl-5-[4-(6,7-dimethoxy-naphthyl-(2)-sulfonyl)-butoxy]-indolinone-2

The above compound was prepared analogously to Example 9 from 3,3-dimethyl-5-[4-(6,7-dimethoxy-naphthyl-(2)-sulfinyl)-butoxy]-indolinone-2 and hydrogen peroxide.
M.p.: 203°–205° C.
Yield: 68% of theory.

EXAMPLE 28

3,3-Dimethyl-5-[4-(4-acetamino-phenylmercapto)-butoxy]-indolinone-2

The above compound was prepared analogously to Example 7 from 3,3-dimethyl-5-(4-chloro-butoxy)-indolinone-2 and 4-acetaminothiophenol.
M.p.: 166°–169° C.
Yield: 74% of theory.

EXAMPLE 29

3,3-Dimethyl-5-[4-(4-acetamino-phenylsulfinyl)-butoxy]-indolinone-2

The above compound was prepared analogously to Example 8 from 3,3-dimethyl-5-[4-(4-acetamino-phenylmercapto)-butoxy]-indolinone-2 and hydrogen peroxide. The raw product was a resinous colorless substance, which for purification was chromatographed over a silica gel column by means of a mixture of ethyl acetate/methylene chloride/ethanol (4.5:4.5:1). $R_f$ value: 0.2. (Silica gel plate with fluorescent material eluant: ethyl acetate/methylene chloride/ethanol (4.5:4.5:1)).
Yield: 76% of theory.

EXAMPLE 30

3,3-Dimethyl-5-[4-(4-acetamino-phenylsulfonyl)-butoxy]-indolinone-2

The above compound was prepared analogously to Example 9 from 3,3-dimethyl-5-[4-(4-acetamino-phenylmercapto)-butoxy]-indolinone-2 and hydrogen peroxide.
M.p.: 183°–184° C.
Yield: 84% of theory.

EXAMPLE 31

3,3-Dimethyl-5-[4-(2-pyridylmercapto)-butoxy]-indolinone-2

The above compound was prepared analogously to Example 7 from 3,3-dimethyl-5-(4-chlorobutoxy)-indolinone-2 and 2-pyridylmercaptane.
M.p.: 101°–103° C.
Yield: 82% of theory.

EXAMPLE 32

3,3-Dimethyl-5-[4-(2-pyridylsulfinyl)-butoxy]-indolinone-2

The above compound was prepared analogously to Example 8 from 3,3-dimethyl-5-[4-(2-pyridylmercapto)-butoxy]-indolinone-2 and hydrogen peroxide. The raw product, a orange-colored resin, was chromatogrphed on a silica gel column with a mixture of ethyl acetate/methylene chloride (1:1).
M.p.: 137°–138° C.
Yield: 80% of theory.

EXAMPLE 33

3,3-Dimethyl-5-[4-(2-pyridylsulfonyl)-butoxy]-indolinone-2

The above compound was prepared analogously to Example 9 from 3,3-dimethyl-5-[4-(2-pyridylsulfinyl)-butoxy]-indolinone-2 and hydrogen peroxide.
M.p.: 89°–90° C.
Yield: 78% of theory.

EXAMPLE 34

3,3-Dimethyl-5-[4-(2-quinolylmercapto)-butoxy]-indolinone-2

The above compound was prepared analogously to Example 7 from 3,3-dimethyl-5-(4-chlorobutoxy)-indolinone-2 and 2-mercaptoquinoline.
M.p.: 129°–130° C.
Yield: 65% of theory.

EXAMPLE 35

3,3-Dimethyl-5-[4-(3,5-dichloro-4-hydroxy-phenylmercapto)butoxy]-indolinone-2

The above compound was prepared analogously to Example 7 from 3,3-dimethyl-5-(4-chloro-butoxy)-indolinone-2 and 3,5-dichloro-4-hydroxy-thiophenol.
M.p.: 170°–171° C.
Yield: 55% of theory.

EXAMPLE 36

3,3-Dimethyl-5-[4-(2-quinolylsulfonyl)-butoxy]-indolinone-2

The above compound was prepared analogously to Example 9 from 3,3-dimethyl-5-[4-(2-quinolylmercapto)-butoxy]-indolinone-2 and hydrogen peroxide with a reaction time of 24 hours. The resinous crude produce was chromatographed on a silica gel column with ethyl acetate/methylene chloride (1:1).
M.p.: 164°–165° C. (from ethyl acetate).
Yield: 67% of theory.

EXAMPLE 37

3,3-Dimethyl-5-[4-(4-methoxy-phenylmercapto)-butoxy]-indolinone-2

The above oompound was prepared analogously to Example 7 from 3,3-dimethyl-5-(5-chloro-butoxy)-indolinone-2 and 4-methoxythiophenol.
M.p.: 122°–123° C.
Yield: 88% of theory.

EXAMPLE 38

3,3-Dimethyl-5-[4-(4-methoxy-phenylsulfinyl)-butoxy]-indolinone-2

The above compound was prepared analogously to Example 8 from 3,3-dimethyl-5-[4-(4-methoxy-phenylmercapto)-butoxy]-indolinone-2 and hydrogen peroxide.
M.p.: 91°–92° C.
Yield: 82% of theory.

EXAMPLE 39

3,3-Dimethyl-5-[4-(4-methoxy-phenylsulfonyl)-butoxy]-indolinone-2

The above compound was prepared analogously to Example 9 from 3,3-dimethyl-5-[4-(4-methoxyphenylmercapto)-butoxy]-indolinone-2 and hydrogen peroxide.
M.p.: 149°–150° C.
Yield: 96% of theory.

EXAMPLE 40

3,3-Dimethyl-5-[4-(6-methoxy-naphthyl-(2)-mercapto)-butoxy]-indolinone-2

The above compound was prepared analogously to Example 7 from 3,3-dimethyl-5-(4-chlorobutoxy)-indolinone-2 and 6-methoxy-thionaphthol-(2).
M.p.: 157°–158° C.
Yield: 75% of theory.

EXAMPLE 41

3,3-Dimethyl-5-[4-(6-methoxy-naphthyl-(2)-sulfinyl)-butoxy]-indolinone-2

The above compound was prepared analogously to Example 8 from 3,3-dimethyl-5-[4-(6-methoxy-naphthyl-(2)-mercapto)-butoxy]-indolinone-2 and hydrogen peroxide.
M.p.: 201°–202° C.
Yield: 93% of theory.

EXAMPLE 42

3,3-Dimethyl-5-[4-(6-methoxy-naphthyl-(2)-sulfonyl)-butoxy]-indolinone-2

The above compound was prepared analogously to Example 9 from 3,3-dimethyl-5-[4-(6-methoxy-naphthyl-(2)-mercapto)-butoxy]-indolinone-2 and hydrogen peroxide.
M.p.: 169°–170° C.
Yield: 90% of theory.

EXAMPLE 43

3,3-Dimethyl-5-[4-(3,5-di-tert.butyl-4-hydroxy-phenylmercapto)-butoxy]-indolinone-2

The above compound was prepared analogously to Example 7 from 3,3-dimethyl-5-(4-chloro-butoxy)-indolinone-2 and 3,5-di-tert.butyl-4-hydroxy-thiophenol.
M.p.: 144°–146° C.
Yield: 83% of theory.

EXAMPLE 44

3,3-Dimethyl-5-[4-(3,5-di-tert.butyl-4-hydroxy-phenylsulfinyl)-butoxy]-indolinone-2

The above compound was prepared analogously to Example 8 from 3,3-dimethyl-5-[4-(3,5-di-tert.butyl-4-hydroxy-phenylmercapto)-butoxy]-indolinone-2 and hydrogen peroxide.
M.p.: 118°–120° C.
Yield: 87% of theory.

EXAMPLE 45

3,3-Dimethyl-5-[4-(3,5-di-tert.butyl-4-hydroxy-phenylsulfonyl)-butoxy]-indolinone-2

The above compound was prepared analogously to Example 9 from 3,3-dimethyl-5-[4-(3,5-di-tert.butyl-4-hydroxy-phenylmercapto)-butoxy]-indolinone-2 and hydrogen peroxide.
M.p.: 87°–89° C.
Yield: 93% of theory.

EXAMPLE 46

3,3-Dimethyl-5-[4-(naphthyl-(2)-mercapto)-butoxy]-indolinone-2

The above compound was prepared analogously to Example 7 from 3,3-dimethyl-5-(4-chloro-butoxy)-indolinone-2 and 2-naphthylmercaptan.
M.p. 116°–117° C.
Yield: 97% of theory.

EXAMPLE 47

3,3-Dimethyl-5-[4-(naphthyl-(2)-sulfinyl)-butoxy]-indolinone-2

The above compound was prepared analogously to Example 8 from 3,3-dimethyl-5-[4-(naphthyl-(2)-mercapto)-butoxy]-indolinone-2 and hydrogen peroxide.
M.p.: 111°–113° C.
Yield: 72% of theory.

EXAMPLE 48

3,3-Dimethyl-5-[4-(naphthyl-(2)-sulfonyl)-butoxy]-indolinone-2

The above compound was prepared analogously to Example 9 from 3,3-dimethyl-5-[4-(naphthyl-(2)-sulfinyl)-butoxy]-indolinone-2 and hydrogen peroxide.
M.p.: 126°–127° C.
Yield: 86% of theory.

EXAMPLE 49

3,3-Dimethyl-5-[4-(4-chlorophenylmercapto)-butoxy]-indolinone-2

The above compound was prepared analogously to Example 7 from 3,3-dimethyl-5-(4-chlorobutoxy)-indolinone-2 and 4-chloro-thiophenol.
M.p.: 124°–126° C.
Yield: 69% of theory.

EXAMPLE 50

3,3-Dimethyl-5-[4-(4-chlorophenylsulfinyl)-butoxy]-indolinone-2

The above compound was prepared analogously to Example 8 from 3,3-dimethyl-5-[4-(4-chlorophenylmercapto)-butoxy]-indolinone-2 and hydrogen peroxide.
M.p.: 128°–130° C.
Yield: 91% of theory.

EXAMPLE 51

3,3-Dimethyl-5-[4-(4-chlorophenylsulfonyl)-butoxy]-indolinone-2

The above compound was prepared analogously to Example 9 from 3,3-dimethyl-5-[4-(4-chlorophenylsulfinyl)-butoxy]-indolinone-2 and hydrogen peroxide.
M.p.: 128°–129° C.
Yield: 88% of theory.

EXAMPLE 52

3,3-Dimethyl-5-[4-(4-bromophenylmercapto)-butoxy]-indolinone-2

The above compound was prepared analogously to Example 7 from 3,3-dimethyl-5-(4-chlorobutoxy)-indolinone-2 and 4-bromo-thiophenol.
M.p.: 125°–127° C.
Yield: 67% of theory.

EXAMPLE 53

3,3-Dimethyl-5-[4-(4-bromophenylsulfinyl)-butoxy]-indolinone-2

The above compound was prepared analogously to Example 8 from 3,3-dimethyl-5-[4-(4-bromophenylmercapto)-butoxy]-indolinone-2 and hydrogen peroxide.
M.p.: 144°–146° C.
Yield: 89% of theory.

EXAMPLE 54

3,3-Dimethyl-5-[4-(4-bromophenylsulfonyl)-butoxy]-indolinone-2

The above compound was prepared analogously to Example 9 from 3,3-dimethyl-5-[4-(4-bromophenyl-mercapto)-butoxy]-indolinone-2 and hydrogen peroxide.
M.p.: 148°–149° C.
Yield: 79% of theory.

EXAMPLE 55

3,3-Dimethyl-5-[4-(4-fluorophenyl-mercapto)-butoxy]-indolin-one-2
The above compound was prepared analogously to Example 7 from 3,3-dimethyl-5-(4-chlorobutoxy)-indolinone-2 and 4-fluoro-thiophenol.
M.p.: 127°–129° C.
Yield: 81% of theory.

EXAMPLE 56

3,3-Dimethyl-5-[4-(4-fluorophenylsulfinyl)-butoxy]-indolinone-2
The above compound was prepared analogously to Example 8 from 3,3-dimethyl-5-[4-(4-fluorophenyl-mercapto)-butoxy]-indolinone-2 and hydrogen peroxide.
M.p.: 79°–81° C.
Yield: 91% of theory.

EXAMPLE 57

3,3-Dimethyl-5-[4-(4-fluorophenylsulfonyl)-butoxy]-indolinone-2
The above compound was prepared analogously to Example 9 from 3,3-dimethyl-5-[4-(4-fluorophenyl-mercapto)-butoxy]-indolinone-2 and hydrogen peroxide.
M.p.: 124°–125° C.
Yield: 81% of theory.

EXAMPLE 58

3,3-Dimethyl-5-[4-(2,5-dichlorophenyl-mercapto)-butoxy]-indolinone-2
The above compound was prepared analogously to Example 7 from 3,3-dimethyl-5-(4-chlorobutoxy)-indolinone-2 and 2,5-dichloro-thiophenol.
M.p.: 67°–69° C.
Yield: 57% of theory.

EXAMPLE 59

3,3-Dimethyl-5-[4-(2,5-dichlorophenylsulfinyl)-butoxy]-indolinone-2
The above compound was prepared analogously to Example 8 from 3,3-dimethyl-5-[4-(2,5-dichlorophenyl-mercapto)-butoxy]-indolinone-2 and hydrogen peroxide.
M.p.: 77°–79° C.
Yield: 88% of theory.

EXAMPLE 60

3,3-Dimethyl-5-[4-(2,5-dichlorophenylsulfonyl)-butoxy]-indolinone-2
The above compound was prepared analogously to Example 9 from 3,3-dimethyl-5-[4-(2,5-dichlorophenylsulfinyl)-butoxy]-indolinone-2 and hydrogen peroxide.
M.p.: 122°–123° C.
Yield: 81% of theory.

EXAMPLE 61

3,3-Dimethyl-5-[4-(4-methylphenyl-mercapto)-butoxy]-indolinone-2
The above compound was prepared analogously to Example 7 from 3,3-dimethyl-5-(4-chlorobutoxy)-indolinone-2 and 4-methylthiophenol.
M.p.: 125°–127° C.
Yield: 74% of theory.

EXAMPLE 62

3,3-Dimethyl-5-[4-(4-methylphenylsulfinyl)-butoxy]-indolinone-2
The above compound was prepared analogously to Example 8 from 3,3-dimethyl-5-[4-(4-methylphenylmercapto)-butoxy]-indolinone-2 and hydrogen peroxide.
M.p.: 125°–126° C.
Yield: 78% of theory.

EXAMPLE 63

3,3-Dimethyl-5-[4-(4-methylphenylsulfonyl)-butoxy]-indolinone-2
The above compound was prepared analogously to Example 9 from 3,3-dimethyl-5-[4-(4-methylphenylmercapto)-butoxy]-indolinone-2 and hydrogen peroxide.
M.p.: 141°–142° C.
Yield: 74% of theory.

EXAMPLE 64

3,3-Dimethyl-5-[5-(4-cyclohexylphenylmercapto)-pentoxy]-indolinone-2
The above compound was prepared analogously to Example 7 from 3,3-dimethyl-5-(5-bromo-pentoxy)-indolinone-2 (m.p.: 80.5°–85.0° C.) and 4-cyclohexylthiophenol.
M.p.: 90°–92° C.
Yield: 94% of theory.

EXAMPLE 65

3,3-Dimethyl-5-[5-(4-cyclohexylphenylsulfinyl)-pentoxy]-indolinone-2
The above compound was prepared analogously to Example 8 from 3,3-dimethyl-5-[5-(4-cyclohexylphenylmercapto)-pentoxy]-indolinone-2 and hydrogen peroxide.
M.p.: 131°–133° C.
Yield: 95% of theory.

EXAMPLE 66

3,3-Dimethyl-5-[3-(4-cyclohexylphenylmercapto)-propoxy]-indolinone-2
The above compound was prepared analogously to Example 7 from 3,3-dimethyl-5-(3-chloropropoxy)-indolinone-2 (m.p.: 68°–70° C.) and 4-cyclohexylthiophenol.
M.p.: 90°–91° C.
Yield: 56% of theory.

EXAMPLE 67

3,3-Dimethyl-5-[3-(4-cyclohexylphenylsulfinyl)-propoxy]-indolinone-2
The above compound was prepared analogously to Example 8 from 3,3-dimethyl-5-[3-(4-cyclohexylphenyl-mercapto)-propoxy]-indolinone-2 and hydrogen peroxide. $R_f$ value: 0.25 (silica gel fluorescent plates; eluant: ethyl acetate/methylene chloride (1:1)).
Yield: 81% of theory.

EXAMPLE 68

3,3-Dimethyl-5-[5-(3,4-dichlorophenylmercapto)-pentoxy]-indolinone-2
The above compound was prepared analogously to Example 7 from 3,3-dimethyl-5-(5-bromo-pentoxy)-indolinone-2 (m.p.: 80.5°–85.0° C.) and 3,4-dichlorothiophenol.

M.p.: 85°–88° C.
Yield: 87% of theory.

EXAMPLE 69

3,3-Dimethyl-5-[5-(3,4-dichlorophenylsulfinyl)-pentoxy]-indolinone-2

The above compound was prepared analogously to Example 8 from 3,3-dimethyl-5-[5-(3,4-dichlorophenylmercapto)-pentoxy]-indolinone-2 and hydrogen peroxide.
M.p.: 125°–127° C.
Yield: 64% of theory.

EXAMPLE 70

3,3-Dimethyl-5-[3-(3,4-dichlorophenylmercapto)-propoxy]-indolinone-2

The above compound was prepared analogously to Example 7 from 3,3-dimethyl-5-(3-chloropropoxy)-indolinone-2 (m.p.: 68°–70° C.) and 3,4-dichlorothiophenol.
M.p.: 90°–91° C.
Yield: 56% of theory.

EXAMPLE 71

3,3-Dimethyl-5-[3-(3,4-dichlorophenylsulfinyl)-propoxy]-indolinone-2

The above compound was prepared analogously to Example 8 from 3,3-dimethyl-5-[3-(3,4-dichlorophenylmercapto)-propoxy]-indolinone-2 and hydrogen peroxide.
M.p.: 131°–133° C.
Yield: 95% of theory.

EXAMPLE 72

3,3-Dimethyl-5-[2-(3,4-dichlorophenylmercapto)-ethoxy]-indolinone-2

The above compound was prepared analogously to Example 7 from 3,3-dimethyl-5-(2-chloroethoxy)-indolinone-2 (m.p.: 151°–152° C.) and 3,4-dichlorothiophenol.
M.p.: 140°–141° C.
Yield: 98% of theory.

EXAMPLE 73

3,3-Dimethyl-5-[2-(3,4-dichlorophenylsulfinyl)-ethoxy]-indolinone-2

The above compound was prepared analogously to Example 8 from 3,3-dimethyl-5-[2-(3,4-dichlorophenylmercapto)-ethoxy]-indolinone-2 and hydrogen peroxide.
M.p.: 150°–151° C.
Yield: 80% of theory.

EXAMPLE 74

3,3-Dimethyl-5-[2-(4-cyclohexylphenyl-mercapto)-ethoxy-indolinone-2

The above compound was prepared analogously to Example 7 from 3,3-dimethyl-5-(2-chloroethoxy)-indolinone-2 (m.p.: 151°–152° C.) and 4-cyclohexylthiophenol.
M.p.: 123°–126° C.
Yield: 96% of theory.

EXAMPLE 75

3,3-Dimethyl-5-[2-(4-cyclohexylphenylsulfinyl)-ethoxy]-indolinone-2

The above compound was prepared analogously to Example 8 from 3,3-dimethyl-5-[2-(4-cyclohexylphenyl-mercapto)-ethoxy]-indolinone-2 and hydrogen peroxide.
M.p.: 141°–143° C.
Yield: 69% of theory.

EXAMPLE 76

3,3-Dimethyl-5-[4-(2,4,6-trimethylphenyl-mercapto)-butoxy]-indolinone-2

The above compound was prepared analogously to Example 7 from 3,3-dimethyl-5-(4-chlorobutoxy)-indolinone-2 and 2,4,6-trimethylthiophenol.
M.p.: 113°–114° C.
Yield: 68% of theory.

EXAMPLE 77

3,3-Dimethyl-5-[4-(2,4,6-trimethylphenyl-sulfinyl)-butoxy]-indolinone-2

The above compound was prepared analogously to Example 8 from 3,3-dimethyl-5-[4-(2,4,6-trimethylphenyl-mercapto)-butoxy]-indolinone-2 and hydrogen peroxide.
M.p.: 96°–97° C.
Yield: 95% of theory.

EXAMPLE 78

3,3-Dimethyl-5-[4-(2,4,6-trimethylphenyl-sulfonyl)-butoxy]-indolinone-2

The above compound was prepared analogously to Example 9 from 3,3-dimethyl-5-[4-(2,4,6-trimethylphenyl-mercapto)-butoxy]-indolinone-2 and hydrogen peroxide.
M.p.: 80°–82° C.
Yield: 83% of theory.

EXAMPLE 79

3,3-Dimethyl-5-[4-(2-methoxyphenyl-mercapto)-butoxy]-indolinone-2

The above compound was prepared analogously to Example 7 from 3,3-dimethyl-5-(4-chlorobutoxy)-indolinone-2 and 2-methoxythiophenol.
M.p.: 98°–100° C.
Yield: 94% of theory.

EXAMPLE 80

3,3-Dimethyl-5-[4-(2-methoxyphenyl-sulfinyl)-butoxy]-indolinone-2

The above compound was prepared analogously to Example 8 from 3,3-dimethyl-5-[4-(2-methoxyphenyl-mercapto)-butoxy]-indolinone-2 and hydrogen peroxide.
M.p.: 109°–110° C.
Yield: 84% of theory.

EXAMPLE 81

3,3-Dimethyl-5-[4-(2-methoxyphenyl-sulfonyl)-butoxy]-indolinone-2

The above compound was prepared analogously to Example 9 from 3,3-dimethyl-5-[4-(2-methoxyphenyl-sulfinyl)-butoxy]-indolinone-2 and hydrogen peroxide.
$R_f$ value: 0.4 (silica gel fluorescent plate; eluant: ethylene chloride/ethanol (9:1)).
Yield: 79% of theory.

EXAMPLE 82

3,3-Dimethyl-5-[4-(2-methyl-4-tert.butylphenly-mercapto)-butoxy]-indolinone-2

The above compound was prepared analogously to Example 7 from 3,3-dimethyl-5-(4-chlorobutoxy)-indolinone-2 and 2-methyl-4-tert.butyl-thiophenol.

M.p.: 99°–101° C.

Yield: 71% of theory.

EXAMPLE 83

3,3-Dimethyl-5-[4-(2-methyl-4-tert.butylphenyl-sulfinyl)-butoxy]-indolinone-2

The above compound was prepared analogously to Example 8 from 3,3-dimethyl-5-[4-(2-methyl-4-tert.butylphenyl-mercapto)-butoxy]-indolinone-2 and hydrogen peroxide.

M.p.: 90°–93° C.

Yield: 91% of theory.

EXAMPLE 84

3,3-Dimethyl-5-[4-(2,3,4,5,6-pentamethylphenyl-mercapto)-butoxy]-indolinone-2

The above compound was prepared analogously to Example 7 from 3,3-dimethyl-5-(4-chlorobutoxy)-indolinone-2 and pentamethyl-thiophenol.

M.p.: 137°–140° C.

Yield: 98% of theory.

EXAMPLE 85

3,3-Dimethyl-5-[4-(2,3,4,5,6-pentamethylphenyl-sulfinyl)-butoxy]-indolinone-2

The above compound was prepared analogously to Example 8 from 3,3-dimethyl-5-[4-(2,3,4,5,6-pentamethylphenyl-mercapto)-butoxy]-indolinone-2 and hydrogen peroxide.

M.p.: 173°–175° C.

Yield: 52% of theory.

EXAMPLE 86

3,3-Dimethyl-5-(4-benzylmercapto-butoxy)-indolinone-2

The above compound was prepared analogously to Example 8 from 3,3-dimethyl-5-(4-chlorobutoxy)-indolinone-2 and benzylmercaptane.

M.p.: 70°–71° C.

Yield: 89% of theory.

EXAMPLE 87

3,3-Dimethyl-5-(4-benzylsulfinyl)-butoxy-indolinone-2

The above compound was prepared analogously to Example 8 from 3,3-dimethyl-5-(4-benzylmercapto-butoxy)-indolinone-2 and hydrogen peroxide.

M.p.: 122°–123° C.

Yield: 32% of theory.

EXAMPLE 88

3,3-Dimethyl-5-(4-benzylsulfonyl-butoxy)-indolinone-2

The above compound was prepared analogously to Example 9 from 3,3-dimethyl-5-(4-benzylsulfinyl-butoxy)-indolinone-2 and hydrogen peroxide.

M.p.: 127°–128° C.

Yield: 80% of theory.

The following examples illustrate a few pharmaceutical dosage unit compositions comprising a compound of the present invention, namely, 3,3-dimethyl-5-[4-(4-tert.butylphenylsulfinyl)-butoxy]-indolinone-2, as active ingredient.

EXAMPLE 89

Tablets Containing 100.0 mg of Active Ingredient

Each tablet was compounded from the following ingredients:

| Component | Amount (mg) |
|---|---|
| Active ingredient | 100.0 |
| Lactose | 80.0 |
| Corn starch | 34.0 |
| Polyvinyl pyrrolidone | 4.0 |
| Magnesium stearate | 2.0 |
| TOTAL: | 220.0 |

Preparation:

The active ingredient, lactose, and corn starch were mixed and homogeneously moistened with an aqueous solution of the polyvinyl pyrrolidone. After screening of the moist mass (mesh size 2.0 mm) and drying at 50° C. in a tray drier, the mixture was again passed through a screen (mesh size 1.5 mm) and the magnesium stearate lubricant was added.

Then the mixture was pressed into tablets.

Weight of tablet: 220 mg

Diameter: 10 mm, biplanar with a facet on both sides and a notch on one side.

EXAMPLE 90

Coated Tablets Containing 50.0 mg of Active Ingredient

The composition of each tablet core was as follows:

| Component | Amount (mg) |
|---|---|
| Active ingredient | 50.0 |
| Lactose | 40.0 |
| Corn starch | 17.0 |
| Polyvinyl pyrrolidone | 2.0 |
| Magnesium stearate | 1.0 |
| TOTAL: | 110.0 |

Preparation:

The granulate was prepared analogously to Example 89.

The mixture was pressed into coated tablet cores.

Weight of core: 110 mg

φ: 8 mm, biconvex The cores were isolated and then covered in a coating vessel according to known processes with pyrrolidone and with a coating consisting essentially of sugar up to 200 mg. The cores were subsequently coated with pure sugar syrup up to 210 mg.

EXAMPLE 91

Gelatin Capsules Containing 100.0 mg of Active Ingredient

Each capsule contained a mixture having the following composition:

| Component | Amount (mg) |
|---|---|
| Active ingredient | 100.0 |
| Corn starch, dried | approx. 130.0 |
| Lactose, pulverized | approx. 87.0 |
| Magnesium stearate | 3.0 |
| TOTAL: | approx. 320.0 |

Preparation:

The active ingredient was mixed with the auxiliary products, and the mixture was passed through a screen of mesh size 0.75 mm and mixed homogeneously in a suitable device. The resulting mixture was filled into hard gelatine capsules of size 1.
Content of capsule: approx. 320 mg
Capsule: hard gelatine capsule size 1.

EXAMPLE 92

Suppositories Containing 150 mg of Active Ingredient

Each suppository had the following composition:

| Component | Amount (mg) |
|---|---|
| Active ingredient | 150.0 |
| Polyethylene glycol 1500 | 550.0 |
| Polyethylene glycol 6000 | 460.0 |
| Polyoxyethylene sorbitane monostearate. | 840.0 |
| TOTAL: | 2000.0 |

Preparation:
The suppository mass was melted, and then the active ingredient was homogeneously dispersed therein. Subsequently the melt was poured into pre-cooled molds.

EXAMPLE 93

Suspension Containing 50 mg of Active Ingredient
One hundred milliliters of suspension had the following composition:

| Component | Amount |
|---|---|
| Active ingredient | 1.0 gm |
| Carboxymethyl cellulose-Na—salt | 0.1 gm |
| Methyl p-hydroxybenzoate | 0.05 gm |
| Propyl p-hydroxybenzoate | 0.01 gm |
| Cane sugar | 10.0 gm |
| Glycerin | 5.0 gm |
| Sorbitol solution (70%) | 20.0 gm |
| Fragrance additive | 0.3 gm |
| Distilled water to | 100.0 ml |

Preparation:
Distilled water was heated up to 70° C., and then, under stirring, methyl p-hydroxybenzoate and propyl p-hydroxybenzoate, as well as glycerin and carboxymethyl cellulose sodium salt, were dissolved therein. After the resulting mixture was cooled to room temperature, the active ingredient was added under stirring, and the entire mixture was homogeneously dispersed. After addition and dissolution of the sugar, the sorbitol solution, and the fragrance additive, the suspension was evaporated into vacuo under stirring.

Five milliliters of suspension contained 50 mg of active ingredient.

Any one of the other compounds embraced by Formula I, or a combination thereof, may be substituted for the particular active ingredient employed in Examples 89 through 93. Likewise, the amount of active ingredient in these illustrative examples may be avried to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

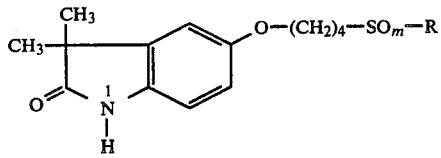

wherein
R is phenyl, 4-chlorophenyl, 4-tert.butylphenyl, 4-methoxyphenyl, 4-(2'-fluorophenyl)-phenyl, 4-cyclohexylphenyl, 3,4-dichlorophenyl, 3,4-dimethoxyphenyl, 3,5-dibromo-4-amino-phenyl, 3,5-dichloro-4-hydroxy-phenyl, 3,5-di-tert.butyl-4-hydroxyphenyl, naphthyl-(2), or 6,7-dimethoxynaphthyl-(2) and
m is 0, 1 or 2.

2. A compound of claim 1,
where
R has the meanings defined in claim 1, and
m is 1.

3. The compound of claim 2 which is 3,3-dimethyl-5-[4-(2'-fluoro-4-biphenylsulfinyl)-butoxy]indolinone-2.

4. The compound of claim 2 which is 3,3-dimethyl-5-[4-(4-amino-3,5-dibromo-phenylsufinyl)-butoxy]indolinone-2.

5. The compound of claim 2 which is 3,3-dimethyl-5-[4-(4-tert.butylphenylsulfinyl)-butoxy]indolinone-2.

6. A pharmaceutical composition for the prophylaxis or treatment of thrombo-embolic diseases or for the treatment of arteriosclerosis which consists essentially of inert, pharmacologically acceptable carrier and an effective amount of a compound of claim 1.

7. A method for the prophylaxis or treatment of thrombo-embolic diseases or for the treatment of arteriosclerosis in a warm-blooded animal which comprises perorally, parenterally, rectally, or topically administering to said animal an effective amount of a compound of claim 1.

* * * * *